(12) United States Patent
Gershony et al.

(10) Patent No.: US 8,632,559 B2
(45) Date of Patent: Jan. 21, 2014

(54) METHOD AND SYSTEM FOR TREATING VALVE STENOSIS

(75) Inventors: Gary Gershony, Piedmont, CA (US); David Doty, Forestville, CA (US)

(73) Assignee: AngioScore, Inc., Fremont, CA (US)

( * ) Notice: Subject to any disclaimer, the term of this patent is extended or adjusted under 35 U.S.C. 154(b) by 0 days.

(21) Appl. No.: 13/236,449

(22) Filed: Sep. 19, 2011

(65) Prior Publication Data

US 2012/0245607 A1    Sep. 27, 2012

Related U.S. Application Data

(60) Provisional application No. 61/384,800, filed on Sep. 21, 2010.

(51) Int. Cl.
*A61B 17/22*   (2006.01)
*A61D 1/02*    (2006.01)

(52) U.S. Cl.
USPC .......................................................... 606/159

(58) Field of Classification Search
USPC ......... 606/194, 195, 198–200, 159; 623/1.14, 623/1.36, 2.11
See application file for complete search history.

(56) References Cited

U.S. PATENT DOCUMENTS

| | | | |
|---|---|---|---|
| 4,986,830 A | 1/1991 | Owens et al. | |
| 5,196,024 A * | 3/1993 | Barath | 606/159 |
| 5,443,446 A | 8/1995 | Shturman | |
| 6,746,463 B1 | 6/2004 | Schwartz | |
| 7,029,483 B2 | 4/2006 | Schwartz | |
| 7,455,652 B2 | 11/2008 | Laird | |
| 7,686,824 B2 | 3/2010 | Konstantino et al. | |
| 7,691,119 B2 | 4/2010 | Farnan | |
| 2002/0010489 A1 * | 1/2002 | Grayzel et al. | 606/194 |
| 2004/0133223 A1 * | 7/2004 | Weber | 606/159 |
| 2004/0243158 A1 | 12/2004 | Konstantino et al. | |
| 2005/0021070 A1 | 1/2005 | Feld et al. | |
| 2005/0021071 A1 | 1/2005 | Konstantino et al. | |
| 2005/0137690 A1 | 6/2005 | Salahieh | |
| 2006/0074484 A1 | 4/2006 | Huber | |
| 2006/0085025 A1 | 4/2006 | Farnan et al. | |
| 2006/0259005 A1 | 11/2006 | Konstantino et al. | |
| 2007/0112422 A1 | 5/2007 | Dehdashtian | |
| 2007/0198047 A1 | 8/2007 | Schon et al. | |
| 2009/0105687 A1 | 4/2009 | Deckman et al. | |
| 2009/0264859 A1 | 10/2009 | Mas | |
| 2009/0306582 A1 | 12/2009 | Granada et al. | |
| 2010/0121372 A1 | 5/2010 | Farnan | |

OTHER PUBLICATIONS

International search report and written opinion dated Jan. 11, 2012 for PCT/2011/052392.

* cited by examiner

*Primary Examiner* — Thomas McEvoy
(74) *Attorney, Agent, or Firm* — James W. Geriak; Sheppard, Mullin, Richter & Hampton LLP

(57) ABSTRACT

A valvuloplasty catheter comprises a balloon or other expansible shell which carries a plurality of scoring elements, typically formed in an elastic, self-closing metal cage. The expansible shell and scoring elements are positioned inside an aortic or other cardiac valve, and the shell expanded to engage the scoring elements against stenotic material which covers the valve leaflets and valve annulus. The scoring elements uniformly distributed force to break up the stenotic material, and the cage further contributes to rapid balloon deflation allowing shortening of the treatment time.

5 Claims, 5 Drawing Sheets

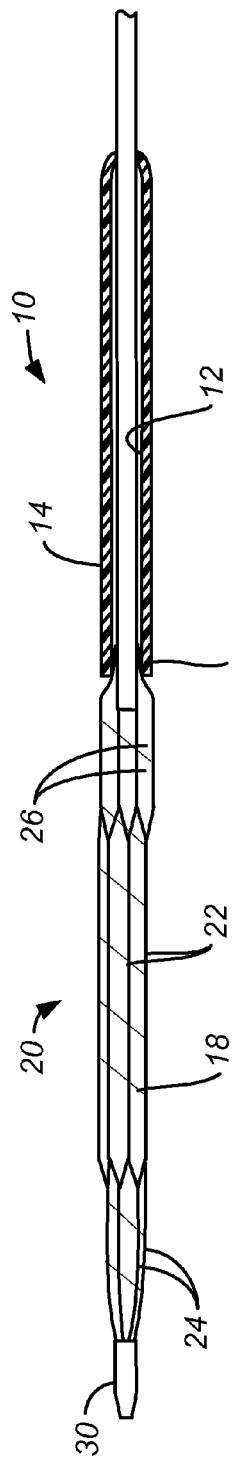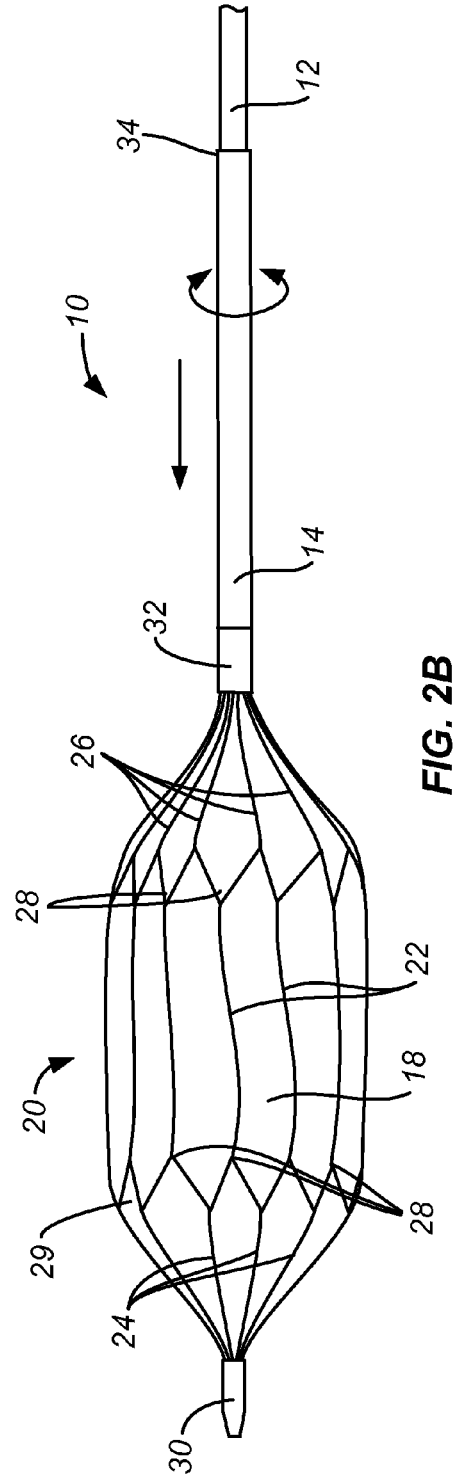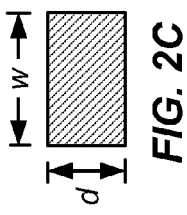

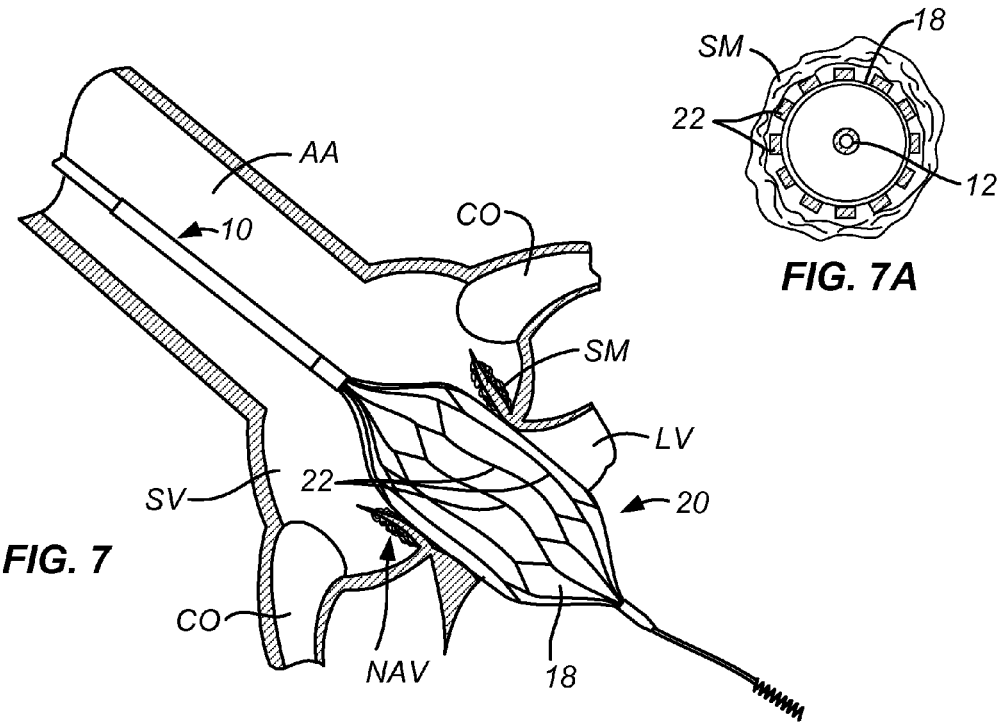
FIG. 7
FIG. 7A
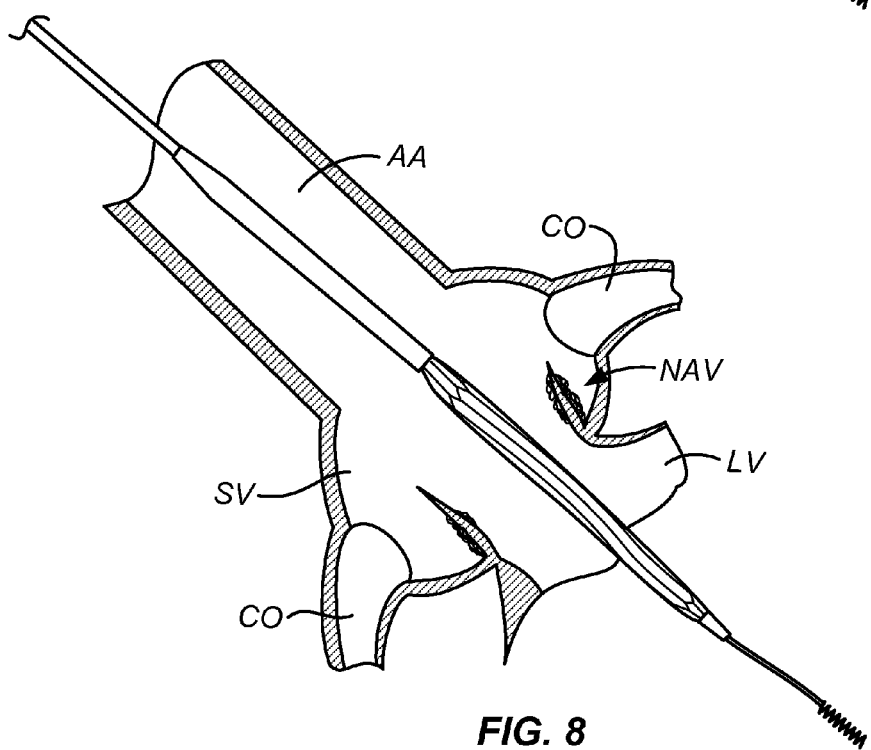
FIG. 8

METHOD AND SYSTEM FOR TREATING VALVE STENOSIS

CROSS REFERENCE TO RELATED APPLICATIONS

This application claims the benefit under 35 U.S.C. 119 of U.S. Provisional Patent Application No. 61/384,800, filed Sep. 21, 2010, the full disclosure of which is incorporated herein by reference.

BACKGROUND OF THE INVENTION

1. Field of the Invention

The present invention relates generally to medical devices and methods. More particularly, the present invention relates to the use of an expandable scoring cage for disrupting stenotic deposits in cardiac valves.

Stenosis of the aortic and other cardiac valves occurs when the valve annulus narrows restricting the flow of blood through the valve when open. This is a particular problem with aortic valve stenosis where the flow of oxygenated blood from the left ventricle to the rest of the body is limited. When the aortic valve is obstructed, the heart must pump at a higher pressure to overcome the increased resistance which can weaken the heart and lead to various symptoms, such as fatigue, chest pain, heart palpitation, heart murmur, and ultimately heart failure. The traditional treatment for aortic valve stenosis has been heart valve replacement through open chest, stopped heart procedures. Recently, percutaneous heart valve replacement has become available. For many patients, however, heart valve replacement is not a realistic choice. Some patients are too weak or ill to undergo such procedures. Other patients are at the beginning stages of valve stenosis where performing a valve replacement procedure might not be justified.

For such patients, it would be desirable to provide alternative therapeutic procedures. Valve anoplasty is one such alternative procedure. A balloon catheter is introduced to the aortic valve, typically through an aortic arch approach, and the balloon inflated within the heart valve to disrupt and loosen stenotic material located on the valve leaflets and in the valve annulus. While such procedures have been clinically employed, they suffer from a number of shortcomings. The principal shortcoming is a lack of effectiveness in some patients. The radial pressure applied by the balloons is not always directed symmetrically, and the balloons can often slip from their original placement within the valve annulus. Both these circumstances limit the effectiveness of conventional valvuloplasty therapy. Moreover, the valvuloplasty balloons must be very large (in order to accommodate the valve annulus), thus requiring a relatively long deflation period. Since the aorta can only be blocked for a short period of time, the need to provide for a lengthy deflation time limits the treatment time in which the balloon can be fully inflated. Additionally, the deflation of such large balloons often leaves a very uneven profile with flaps and portions of the balloon extending radially outwardly. The removal of such structures from the valve annulus can damage the fragile valve leaflets as well as the vasculature through which the catheter is removed. Additionally, valvuloplasty has generally been limited to the treatment of aortic valves.

For these reasons, it would be desirable to provide improved apparatus and methods for performing cardiac valve anioplasty. It would be particularly useful if the methods and apparatus provided for more effective treatment of cardiac valve stenoses, not only in the aorta but in other cardiac valves as well, such as the mitral valve and the pulmonary valve. It would be further desirable to provide valvuloplasty balloons which are capable of applying force symmetrically about their perimeter in order to more effectively treat and fracture stenotic material surrounding the valve annulus. It would be still further desirable if the valvuloplasty balloons were able to resist slippage while inflated, thus improving effectiveness and reducing the risk of left ventricular perforations. It would be still further useful if the valvuloplasty balloons were adapted for rapid deflation so that the period of inflation intended to treat the valve could be prolonged. Additionally, it would be useful if the valvuloplasty balloons folded in a regular manner with a low profile to facilitate removal of the balloons and reduce the risk of trauma to the valve leaflets or other harder vascular structures. At least some of these objectives will be met by the invention as described herein below.

2. Description of the Background Art

Catheters for treating cardiac valve stenoses are described in the following U.S. patents and Published Applications: U.S. Pat. Nos. 4,986,830; 5,443,446; 6,746,463; 7,029,483; 7,455,652; US 2005/0137690; and 2006/0074484. Commonly owned patents and pending applications which relate to the invention herein include: U.S. Pat. Nos. 7,686,824; 7,691,119; U.S. 2004/0243158; 2005/0021071; 2005/0021070; 2006/0259005; 2006/0085025; 2009/0105687; and 2010/0121372, the full disclosures of which are incorporated herein by reference.

BRIEF SUMMARY OF THE INVENTION

The present invention provides improved apparatus and methods for performing valvuloplasty of the aortic and other cardiac valves, such as the pulmonary valve and the mitral valve. Valvuloplasty is the treatment of stenotic cardiac valves by balloon expansion within the valve annulus. Such balloon expansion can open the valve and increase the area available for blood flow by fracturing and displacing stenotic material, such as calcified plaque, which covers the valve leaflets and/or the valve annulus. Such stenotic valves become stiff such that functioning of the valve leaflets deteriorates, including a reduced opening of the leaflets available to allow blood flow during ventricular systole.

The present invention provides for placement of scoring elements over the exterior surface of a balloon or other expansible shell. The scoring elements, which typically number from six to twenty, are preferably uniformly distributed over the outer surface of the balloon so that they concentrate forces uniformly over the circumference of the valve annulus when the balloon is inflated. Such uniformly concentrated forces are able to effectively fracture and displace the stenotic material to increase the area of the annulus available for blood flow and often to improve the ability of the valve leaflets to function. Additionally, when the scoring elements are incorporated in a self-closing elastic cage which is placed over the balloon, the cage is able to improve balloon deflation characteristics so that the balloon deflates both more rapidly and more uniformly so that balloon flaps and other elements are not exposed during withdrawal of the balloon from the valve annulus and vasculature. The scoring elements also help to stabilize the balloon within the valve annulus during balloon inflation to inhibit slippage which can both reduce the effectiveness of the treatment and expose the valve annulus and surrounding tissue to damage.

In a first aspect of the present invention, a method for treating cardiac valve stenoses comprising positioning an expansible shell inside a stenosed cardiac valve annulus. The shell is expanded to engage a plurality of scoring elements present on an external surface of the shell against the annulus. The shell expansion is maintained for a time sufficient for the scoring elements to disrupt the stenoses, after which time the shell is contracted and removed from the valve annulus together with the scoring elements.

Positioning the expansible shell typically comprises advancing a catheter which carries the expansible shell and scoring elements over the aortic arch and into the aortic valve annulus. The shell expansion will typically be maintained in a period of time from 1 second to 10 seconds, usually from 1 second to 4 seconds, typically for about 2 seconds. When using an inflatable balloon, expanding the shell comprising expanding the balloon, and the scoring elements are typically provided as axial struts in an elastic metal cage surrounding but unattached to the inflatable balloon. The cage is elastically biased to close over the balloon as the balloon is inflated, thus both decreasing the deflation time and improving the rewrap characteristics of the balloon over the placement catheter. In the exemplary embodiments, the balloon is non-distensible and inflated to a pressure in the range from 1 atmosphere to 12 atmospheres, preferably from 4 atmospheres to 12 atmospheres, typically about 8 atmospheres. The balloon will usually carry from six to twenty scoring elements and will be inflated to a diameter in the range from twenty millimeters to thirty millimeters, depending on the size of the valve annulus being treated.

In a second aspect, the present invention provides devices for treating cardiac valve stenoses. The devices comprise a shaft having a proximal end and a distal end and an expansible shell carried on a distal region of the shaft. A plurality of scoring elements are carried by the expansible shell, typically over its exterior surface. The expansible shell typically has a length and expanded diameter selected to fully occupy an adult human cardiac valve annulus, typically the aortic valve annulus, and said scoring elements have flat radially outward surfaces for engaging the stenotic material when inflated within a stenosed cardiac valve.

The shaft may be adapted to be introduced over the aortic arch to position the expansible shell in the aortic or other cardiac valve annulus. The expansible shell is preferably a non-distensible inflatable balloon having an inflated diameter (when fully inflated) in the range from twenty millimeters to thirty millimeters. The length of the inflatable balloon will be relatively short, typically in the range from two centimeters to four centimeters. Such a short length may be used because the balloon with the scoring elements thereon is much less likely to be axially displaced when inflated than is a bare balloon. The balloon will typically carry from six to twenty scoring elements, preferably from eight to sixteen scoring elements, which scoring elements extend from a proximal end to a distal end of the balloon and are evenly circumferentially spaced-apart over an exterior surface of the balloon.

The scoring elements are typically formed as axial struts in an elastic metal cage structure. The cage structure is coupled to the catheter shaft but not attached to the expansible balloon. The cage is elastically biased to close to a diameter in the range from three millimeters to seven millimeters when the shell is unexpanded.

In an exemplary embodiment, the elastic metal cage structure comprises a plurality of circumferentially arranged, axially elongated hexagonal cells, where each cell has a proximal connection point and a distal connection at longitudinally opposed ends of the cell. Axial struts are connected to each of the connection points, and the struts are used to connect the cage structure to the catheter shaft. At the distal end, the axial struts are connected directly to the catheter shaft. In contrast, at the proximal end, the axial struts are connected to a compliance tube, where the compliance tube is disposed coaxially over the catheter shaft and attached to the catheter shaft only at a proximal end of the compliance tube. The axial connector links at the proximal end of the elastic metal cage structure are attached to a distal end of the compliance tube. In this way, the compliance tube can accommodate both axial foreshortening of the cage as the balloon is radially expanded as well as to accommodate any rotational, torsional forces experienced by the cage structure as the balloon is expanded.

The scoring elements have dimensions particularly selected to score stenotic material present on cardiac valves. Typically, the scoring elements have rectangular cross-sections with a height (thickness) in the radial direction in the range from 0.1 millimeters to 0.4 millimeters, usually 0.15 millimeters to 0.25 millimeters, and a width in the circumferential direction in the range from 0.25 millimeters to 0.5 millimeters, preferably from 0.3 millimeters to 0.4 millimeters.

BRIEF DESCRIPTION OF THE DRAWINGS

FIGS. 2A and 2B illustrate an expansible shell of the valvuloplasty catheter of FIG. 1 carrying a self-closing elastic cage comprising a plurality of scoring elements, where the balloon and cage are in their contracted configuration in FIG. 2A and in their expanded configuration in FIG. 2B.

FIG. 2C is a cross-sectional view of an individual scoring element of the cage of FIGS. 1, 2A, and 2B.

FIGS. 5-8 and 7A illustrate use of the valvuloplasty catheter of FIG. 1 in treating an aortic valve in accordance with the principals of the present invention.

DETAILED DESCRIPTION OF THE INVENTION

Figure 1:
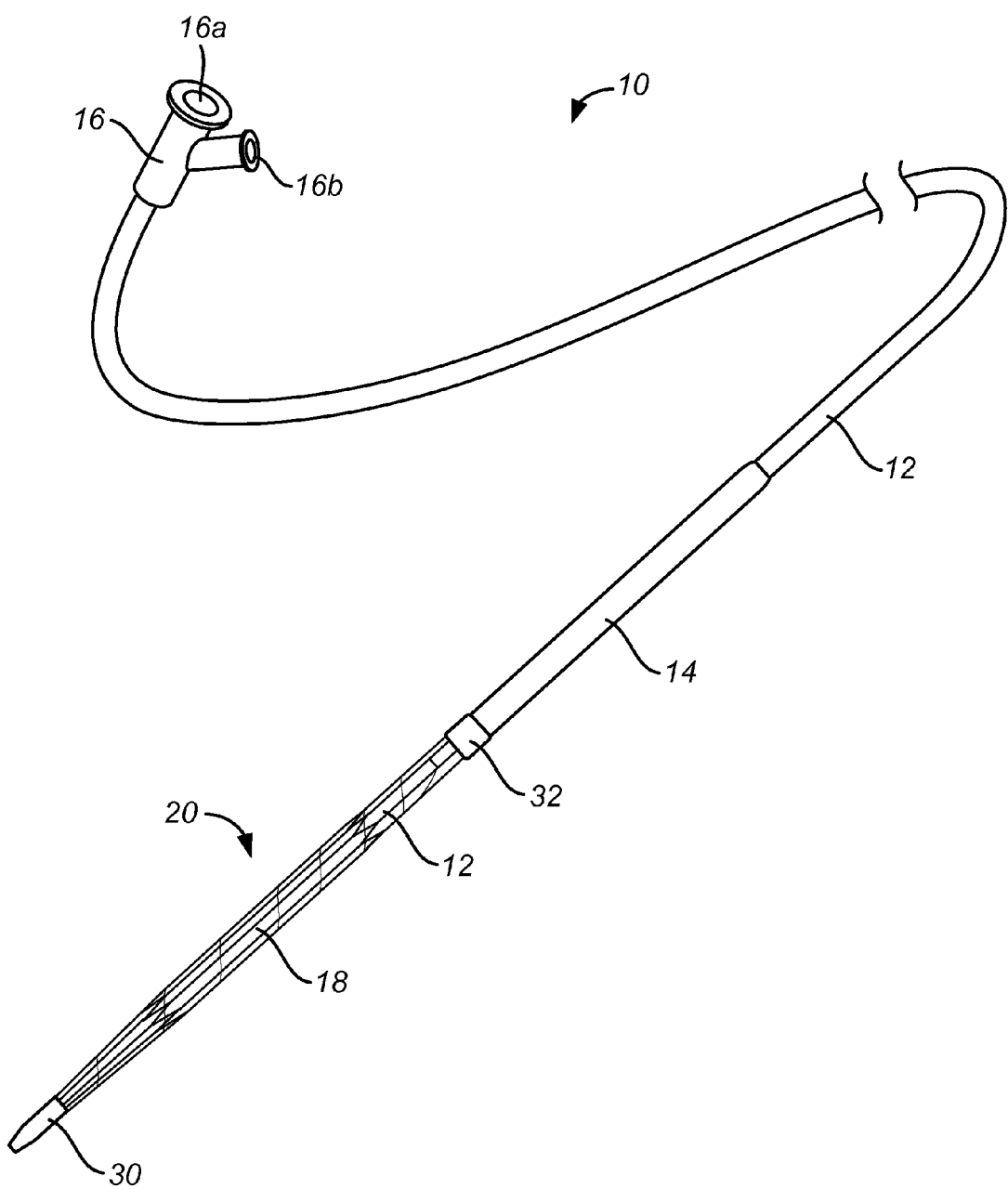
FIG. 1 is a prospective view of a valvuloplasty catheter constructed in accordance with the principals of the present invention.

A valvuloplasty catheter 10 constructed in accordance with the principals of the present invention is illustrated in FIGS. 1, 2A, and 2B. The valvuloplasty catheter 10 comprises a shaft 12 having a compliance tube 14 coaxially disposed over a distal portion thereof. A proximal hub 16 includes an axial guide wire port 16a and a side balloon inflation port 16b. The guide wire port 16a attaches to a guide wire lumen which extends axially over the entire length of catheter shaft 12. The balloon inflation port 16b connects to an inflation lumen, typically formed in a wall of the shaft 12.

An expansible shell 18 is located at the distal end of the catheter shaft 12 and connected to receive inflation medium from the inflation lumen in the shaft which is connected to port 16b. In this way, the balloon can be inflated from a contracted or non-inflated configuration, as shown in FIG. 2A, to a fully inflated configuration, as shown in FIG. 2B.

An expansible metal cage 20 is mounted over the expansible shell (typically an inflatable balloon) 18 so that it expands with the inflated shell or balloon 18, as shown in FIG. 2B, and self-closes over the balloon, as shown in the contracted configuration of FIG. 2A. The elastic metal cage is typically formed from a highly elastic metal, such as nitinol or spring stainless steel, and may typically be formed by laser cutting of a nitinol or stainless steel hypo tube.

In a preferred configuration, the elastic metal cage will comprise hexagonal cells which extend over the middle of the expansible shell when inflated, as best seen in FIG. 2B. The hexagonal cells comprise parallel (axially aligned) scoring elements 22 which are the components which engage and score the stenotic material in the valve annulus when the shell 18 is expanded, as will be described in more detail with FIGS. 6-8 below. In order to maintain an equal circumferential spacing of the scoring elements 22, each end of the scoring element is connected at a connection point 28 to points on a zig zag ring 29 which are in turn connected to distal connecting links 24 at the distal end of the cage and proximal connecting links 26 at the proximal end of the cage. The distal connecting links 24, in turn, are attached to the catheter shaft 12 by a distal collar 30, while the proximal connector links 26 are connected to the compliance tube 14 by a proximal collar 32. The compliance tube 14 is unattached to the catheter shaft 12 except for an attachment point 34 at its proximal end. In this way, when the expansible shell 18 is inflated or otherwise radially expanded, the compliance tube 14 can elongate (in the direction of the linear arrow in FIG. 2B) to accommodate any foreshortening and can also torque or rotate, as shown by the circular arrow in FIG. 2B.

Figure 3:
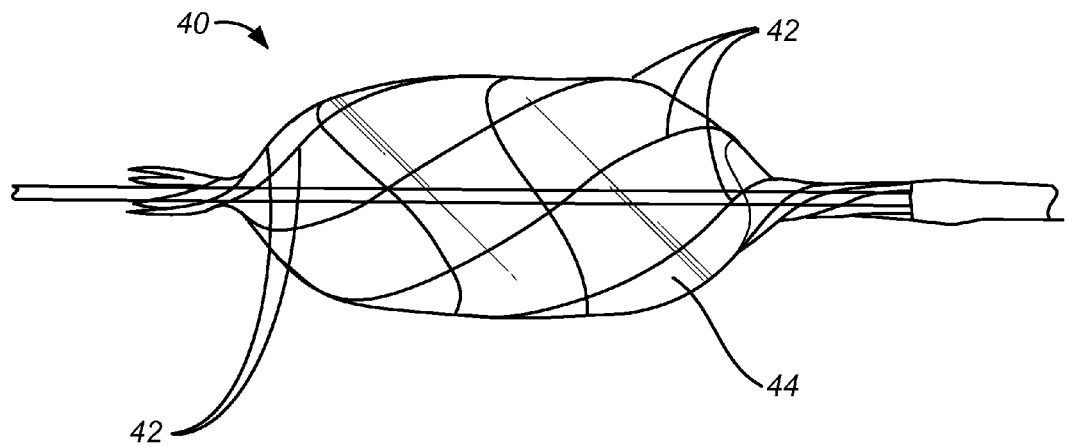
FIGS. 3 and 4 illustrate alternative self-closing cage configurations in accordance with the principals of the present invention.
Figure 4:
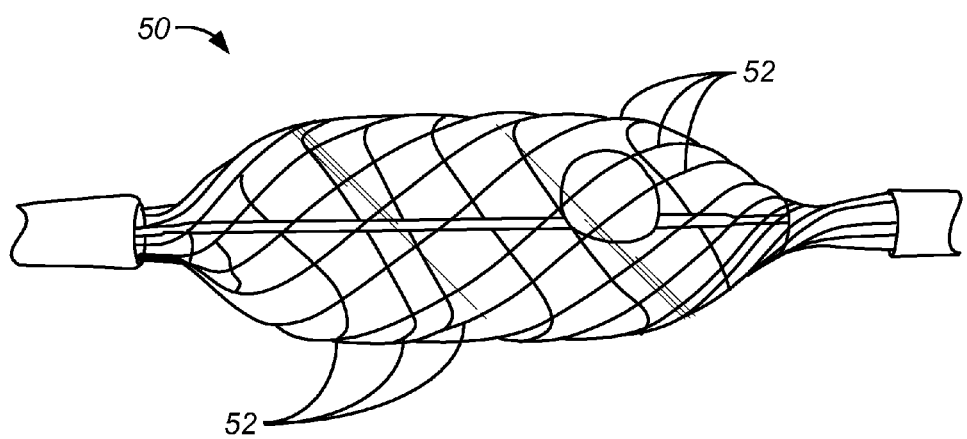

Although the illustrated structure of elastic metal cage 20 is presently preferred as it effectively maintains equal circumferential spacing of the scoring elements 22 as the shell 18 is inflated or otherwise expanded, other shell designs could be employed, such as those having helical scoring elements, as illustrated in FIGS. 3 and 4. In FIG. 3, a cage 40 comprising six helical scoring elements 42 disposed over an inflatable balloon 44. The construction of the catheter which carries balloon 44 and cage 40 will generally be the same as that described with respect to the catheter of FIG. 1. FIG. 4 also describes an expansible cage 50 having a plurality of helical scoring elements 52 where the principal difference is that cage 50 includes twelve scoring elements in contrast to the six scoring elements of cage 40 of FIG. 3.

Figure 5:
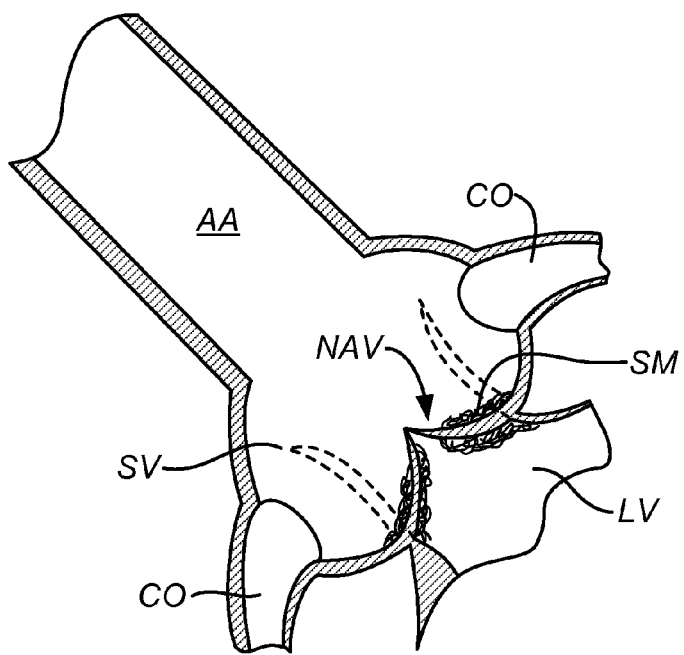

Referring now to FIGS. 5-8, use of the valvuloplasty catheter 10 of FIG. 1 in treating a stenosed aortic valve will be described. The stenosed aortic valve NAV is illustrated in FIG. 5, where the stenotic material SM is present on both the valve leaflets and the valve annulus. While the valve can function, the ability of the valve leaflets to fully open and close is hindered, limiting the blood flow through the open valve and/or allowing leakage through the closed valve. The aortic valve NAV is at the base of the aortic arch AA and adjacent to the Sinus of Valsalva SV. The coronary arteries open off the coronary ostia CO, and the valve NAV opens to permit blood flow from the left ventricle LV into the aortic arch.

Figure 6:
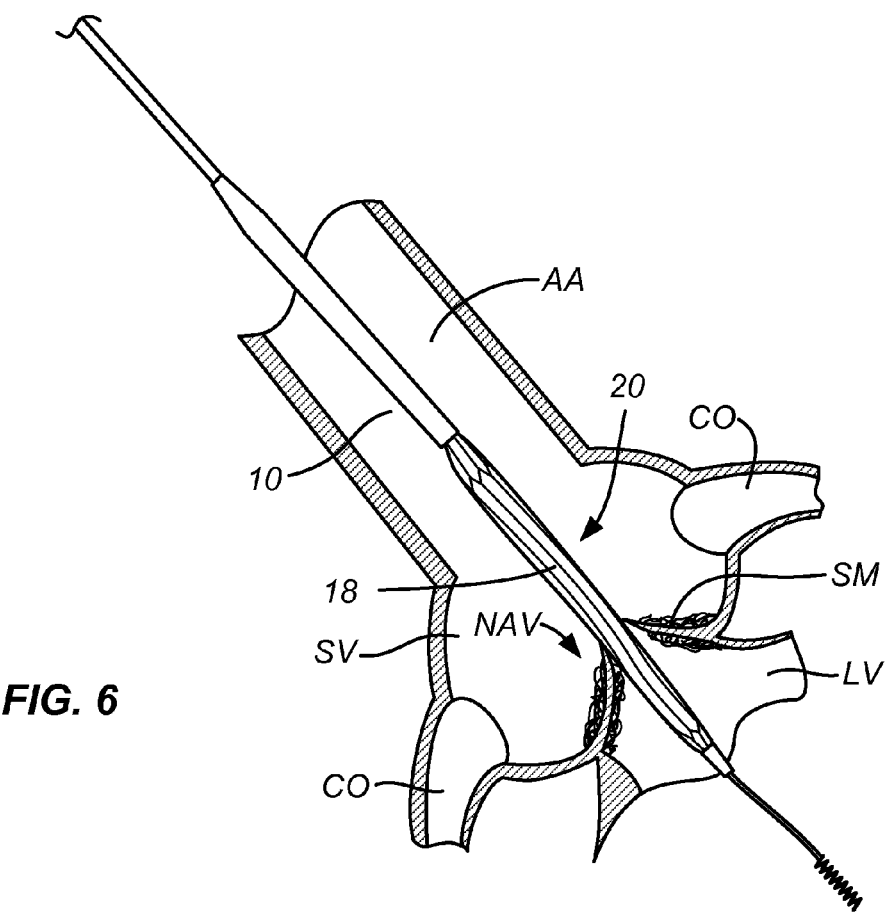

Referring now to FIG. 6, the valvuloplasty catheter 10 is introduced so that the elastic metal cage 20 carried on the expansible shell/balloon 18 is introduced through the valve leaflets into the annulus of the aortic valve NAV. After the catheter 10 is properly positioned, as shown in FIG. 7, the expansible shell 18 is inflated to engage the individual scoring elements 22 against the stenotic material SM around the valve annulus, as shown in FIG. 7A. Note that the cross-sections of the scoring elements 22 are not shown to scale and are actually smaller relative to the expansible shell 18 than illustrated.

After inflating the balloon for a desired period of time, typically from 1 second to 10 seconds, usually from 1 second to 4 seconds, the balloon is rapidly deflated so that the elastic metal cage closes over the balloon, rewrapping the balloon in a compact package, as shown in FIG. 8. Catheter 10 may then be withdrawn and the treatment is completed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A device for treating cardiac valve stenoses, said device comprising:
   a shaft having proximal and distal ends;
   an expansible shell carried on a distal region of the shaft;
   a plurality of nondeployable scoring elements coupled to said shaft but not attached to the expansible shell;
   wherein the expansible shell has a length and expanded diameter selected to fully occupy an adult human cardiac valve annulus and said scoring elements have flat radially outward surfaces;
   wherein the shaft is a catheter shaft adapted to be introduced over the aortic arch to position the expansible shell in the cardiac valve annulus;
   wherein the expansible shell is a nondistensible inflatable balloon having an inflated diameter in the range from 20 mm to 30 mm;
   wherein the inflatable balloon has a length in the range from 2 cm to 4 cm;
   wherein from 5 to 20 scoring elements extend from a proximal end to a distal end of the balloon and are evenly circumferentially spaced apart over an exterior balloon surface;
   wherein the scoring elements are struts in an elastic metal cage structure and parallel to its axis, wherein the cage structure is coupled to the catheter shaft but not attached to the balloon, wherein the cage is elastically biased to contract when the balloon is not inflated;
   wherein the elastic metal cage structure comprises circumferentially arranged elongated hexagonal cells which are parallel to the axis, wherein each cell has a proximal connection point to a proximal ring and a distal connection point to a distal ring and where the struts extend between said connection points;
   wherein the cage further comprises distal connector links which extend between the distal connection point and the catheter shaft to secure the cage to the catheter shaft; and
   further comprising a compliance tube having a distal end coupled to proximal connector links of the cage and a proximal end attached to the catheter shaft, wherein the compliance tube is adapted to accommodate axial elongation and circumferential rotation of the cage structure.

2. A device as in claim 1, wherein the scoring elements have a rectangular cross-section with a height in the radial direction in the range from 0.1 mm to 0.4 mm and a width in the circumferential direction in the range from 0.25 mm to 0.5 mm.

3. A device as in claim 1, wherein the elastically biased cage is capable of improving balloon deflation characteristics by causing the balloon to deflate more rapidly and more uniformly.

4. A device as in claim 1, wherein the elastically biased cage is capable of contracting to a diameter in the range of from 3 mm to 7 mm.

5. A device according to claim 1, wherein at least one of said rings has a zig zag shape.

* * * * *

UNITED STATES PATENT AND TRADEMARK OFFICE
CERTIFICATE OF CORRECTION

PATENT NO.         : 8,632,559 B2
APPLICATION NO.    : 13/236449
DATED              : January 21, 2014
INVENTOR(S)        : Gary Gershony et al.

Page 1 of 1

It is certified that error appears in the above-identified patent and that said Letters Patent is hereby corrected as shown below:

In the Specification

Column 1, line 38, "anoplasty" should read --angioplasty--.

Column 1, line 65, "anioplasty" should read --angioplasty--.

Column 4, lines 24, 34, 38 and 43, each occurrence of "principals" should read --principles--.

Signed and Sealed this
Thirteenth Day of May, 2014

Michelle K. Lee
*Deputy Director of the United States Patent and Trademark Office*